(12) United States Patent
Kim et al.

(10) Patent No.: US 10,918,968 B2
(45) Date of Patent: Feb. 16, 2021

(54) SELECTIVE DISTILLATION APPARATUS AND DISTILLATION METHOD

(71) Applicant: LG CHEM, LTD., Seoul (KR)

(72) Inventors: Tae Woo Kim, Daejeon (KR); Sung Kyu Lee, Daejeon (KR); Sung Kyun Kim, Daejeon (KR); Joon Ho Shin, Daejeon (KR); Yeon Uk Choo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 321 days.

(21) Appl. No.: 16/068,041

(22) PCT Filed: Sep. 6, 2017

(86) PCT No.: PCT/KR2017/009739
§ 371 (c)(1),
(2) Date: Jul. 3, 2018

(87) PCT Pub. No.: WO2018/052217
PCT Pub. Date: Mar. 22, 2018

(65) Prior Publication Data
US 2020/0276517 A1    Sep. 3, 2020

(30) Foreign Application Priority Data

Sep. 13, 2016    (KR) .................. 10-2016-0118045

(51) Int. Cl.
| | | |
|---|---|---|
| *B01D 3/14* | (2006.01) | |
| *B01D 3/42* | (2006.01) | |
| *B01D 3/00* | (2006.01) | |
| *B01D 3/32* | (2006.01) | |
| *C07C 7/04* | (2006.01) | |

(52) U.S. Cl.
CPC .......... *B01D 3/4255* (2013.01); *B01D 3/008* (2013.01); *B01D 3/143* (2013.01); *B01D 3/322* (2013.01); *B01D 3/4205* (2013.01); *C07C 7/04* (2013.01)

(58) Field of Classification Search
CPC ........ B01D 3/008; B01D 3/143; B01D 3/322; B01D 3/4205; B01D 3/4255; C07C 7/04
See application file for complete search history.

(56) References Cited

U.S. PATENT DOCUMENTS

| | | | | |
|---|---|---|---|---|
| 3,309,288 | A * | 3/1967 | Butterbaugh, III | .... B01D 3/425 203/1 |
| 3,420,748 | A * | 1/1969 | Lupfer | .................. B01D 3/425 203/1 |
| 3,555,837 | A * | 1/1971 | McClintock | ......... B01D 3/4211 62/625 |

(Continued)

FOREIGN PATENT DOCUMENTS

| | | |
|---|---|---|
| JP | 2015-100724 A | 6/2015 |
| KR | 10-2014-0063455 A | 5/2014 |

(Continued)

*Primary Examiner* — Jonathan Miller
(74) *Attorney, Agent, or Firm* — Dentons US LLP

(57) ABSTRACT

The present application relates to a selective distillation apparatus and a distillation method, which provides a distillation apparatus capable of switching between a serial connection mode and a parallel connection mode on the situation, thereby enabling selective operation of high-efficiency operation and high-capacity operation.

9 Claims, 3 Drawing Sheets

(56) References Cited

U.S. PATENT DOCUMENTS

| | | | | |
|---|---|---|---|---|
| 4,306,942 | A * | 12/1981 | Brush | B01D 3/001 |
| | | | | 203/19 |
| 4,371,427 | A * | 2/1983 | Holler | B01D 3/40 |
| | | | | 203/3 |
| 4,961,826 | A * | 10/1990 | Grethlein | B01D 1/2856 |
| | | | | 202/154 |
| 5,252,187 | A * | 10/1993 | Ohtsu | B01D 1/26 |
| | | | | 159/24.2 |
| 7,867,365 | B2 * | 1/2011 | Brown | B01D 3/322 |
| | | | | 203/19 |
| 10,022,648 | B2 * | 7/2018 | Maedebach | B01D 3/143 |
| 10,486,080 | B2 * | 11/2019 | Choo | C07C 45/53 |
| 2007/0017291 | A1 | 1/2007 | Cypes et al. | |
| 2015/0143845 | A1 * | 5/2015 | Wakabayashi | F25J 1/0022 |
| | | | | 62/630 |
| 2016/0251297 | A1 * | 9/2016 | Bernardin | B01D 11/0446 |
| | | | | 203/8 |
| 2017/0203230 | A1 * | 7/2017 | Raiser | B01D 3/007 |

FOREIGN PATENT DOCUMENTS

| | | |
|---|---|---|
| KR | 10-2015-0026127 A | 3/2015 |
| KR | 10-2016-052416 A | 5/2016 |

\* cited by examiner

[Figure 1]
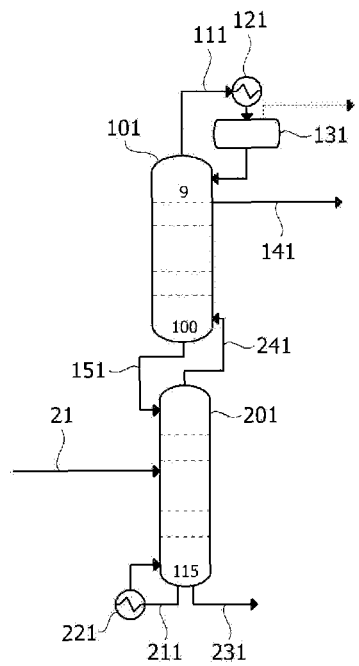
[Figure 2]
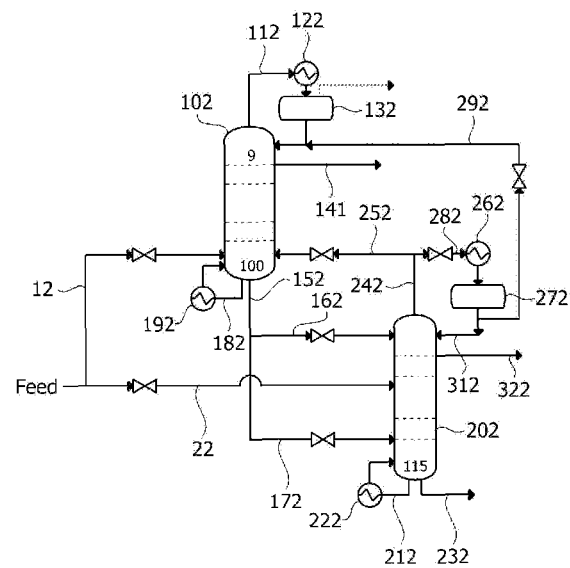

[Figure 3]
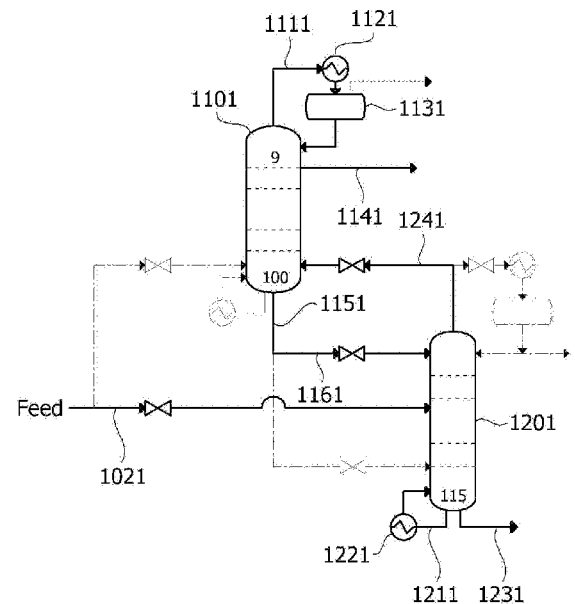
[Figure 4]
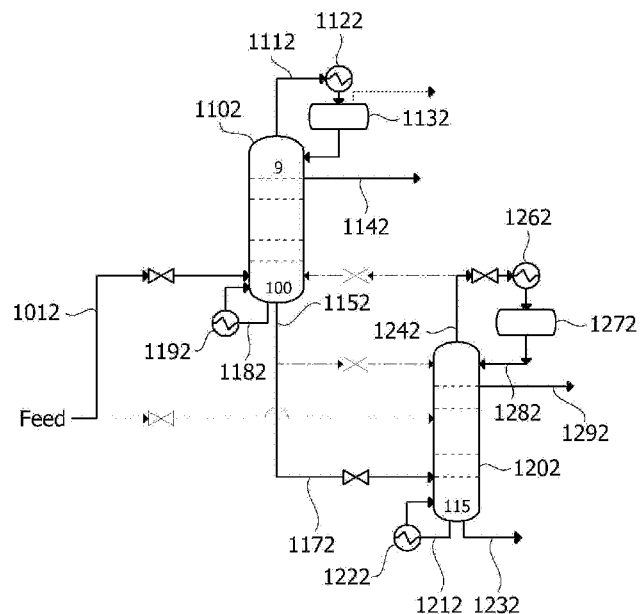

[Figure 5]
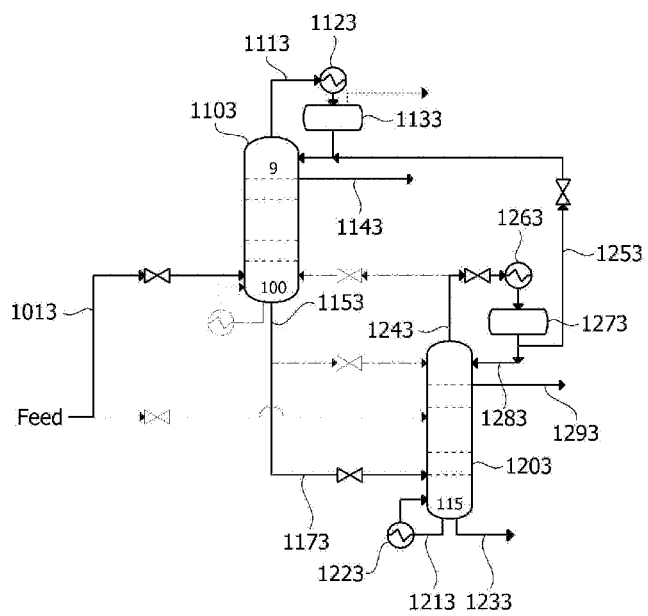

SELECTIVE DISTILLATION APPARATUS AND DISTILLATION METHOD

This application is a 35 USC § 371 National Stage entry of International Application No. PCT/KR2017/009739, filed on Sep. 6, 2017, and claims priority to Korean Application No. 10-2016-0118045, filed on Sep. 13, 2016, all of which are incorporated by reference in their entirety herein.

TECHNICAL FIELD

The present invention relates to a selective distillation apparatus capable of switching between high-efficiency operation and high-capacity operation to each other using two distillation columns and a distillation method using the selective distillation apparatus.

BACKGROUND ART

Various raw materials such as crude oil are usually a mixture of many chemical substances in many cases, where the mixture is rarely used in the industry as such and usually used after being separated into each compound. A typical chemical process for separating the mixture is a distillation process.

In general, the distillation process evaporates and separates the mixed materials of a binary system or more present in the feedstock by the difference in boiling points. As the distillation apparatus used in this distillation process, a distillation column, a rectifying column, a stripping column and a stripping bath, etc. are used, where a low-boiling substance is discharged in the form of overhead vapor from the upper part of the distillation apparatus and a high boiling substance is separated in the form of bottom condensate from the lower part of the distillation apparatus.

The distillation column used in the distillation process should satisfy the minimum number of required stages according to the mixture to be separated, and in the case of a distillation column requiring high number of stages, there are cases where two columns are connected in series and run like one column. FIG. 1 is a schematic view showing one example of a distillation apparatus in which two distillation columns are connected in series. When the distillation columns are connected in series and run as in FIG. 1, the same effect as operating the distillation column having high number of stages can be obtained, but there is a limitation that cannot but have a processing capacity as much as one tower using two towers.

DISCLOSURE

Technical Problem

The present application relates to a selective distillation apparatus, which is intended to provide a distillation apparatus capable of switching between high-efficiency operation and high-capacity operation to each other depending on the situation.

Technical Solution

The present application relates to a selective distillation apparatus, which is characterized in that it is constituted so as to be capable of switching between high-efficiency operation in a serial connection mode and high-capacity operation in a parallel connection mode to each other by connecting two distillation columns.

For example, the selective distillation apparatus according to the present application may comprise a first distillation column equipped with a top reflux device and a bottom reboiler, wherein a top outlet and a bottom outlet are formed, an upper inlet and an upper outlet are formed and a lower inlet is formed; a second distillation column equipped with a top reflux device and a bottom reboiler, wherein a top outlet and a bottom outlet are formed and an upper inlet and a lower inlet are formed; a piping system and a control part.

The piping system may comprise: a first supply line capable of supplying a raw material to the first distillation column; a second supply line capable of supplying a raw material to the second distillation column; a first discharge line capable of discharging a top product or an upper product of the first distillation column; a second discharge line capable of discharging a top product of the second distillation column; a first connecting line connecting the bottom outlet of the first distillation column and the lower inlet of the second distillation column; a second connecting line connecting the bottom outlet of the first distillation column and the upper inlet of the second distillation column; and a third connecting line connecting the top outlet of the second distillation column and the lower inlet of the first distillation column.

The control part may adjust at least one of the reflux devices, the reboilers, the supply lines, the discharge lines, and the connecting lines to an activated or inactivated state.

Also, in one example, the piping system may further comprise a fourth connecting line connecting the top outlet of the second distillation column and the upper inlet of the first distillation column.

Furthermore, the present application can provide a distillation method using the selective distillation apparatus.

Advantageous Effects

According to the selective distillation apparatus of the present application, two distillation columns can be connected in the serial connection mode and the parallel connection mode depending on the situation, and the serial connection mode and the parallel connection mode can be switched to each other. The thermodynamic efficiency can be improved through the serial connection mode to enable a high-efficiency operation, and the throughput of the distillation column can be greatly increased through the parallel connection mode to enable a high-capacity operation.

In addition, the selective distillation apparatus according to the present application can switch between the serial connection mode and the parallel connection mode continuously without shutting the serial connection mode and the parallel connection mode down, thereby reducing the economic loss that may occur upon the shutdown.

BRIEF DESCRIPTION OF DRAWINGS

FIG. 1 is a schematic view showing one example of a distillation apparatus in which two columns are connected in series.

FIG. 2 is a schematic view showing one example of a selective distillation apparatus according to the present application.

FIG. 3 is a schematic view showing a serial connection mode of a selective distillation apparatus according to one embodiment of the present application;

FIGS. 4 and 5 are schematic views showing a parallel connection mode of a selective distillation apparatus according to one embodiment of the present application.

BEST MODE

In this specification, the term 'and/or' is used as a meaning to include at least one or more of components listed before and after.

In this specification, the term such as "first," "second," "one side," and "other side" is used to distinguish one component from another component, where each component is not limited by the terms. Hereinafter, in explaining the present application, detailed descriptions of known general functions or configurations are omitted.

In this specification, the term "piping system" may mean a structure which comprises pipes or lines connecting devices, where the "line" may be substantially the same as the pipe, the term "stream" may mean a movement of a fluid through the line or pipe, and the line, pipe and stream herein may share the same reference numeral.

In this specification, the "open" and "activation" may refer to a state where a fluid can flow through operation of a valve attached to a line or pipe, or a state where an equipment attached to a device can operate, and the "closure" and "inactivation" may refer to a state where a fluid cannot flow through operation of a valve attached to a line or pipe, or a state where an equipment attached to a device does not operate.

Hereinafter, the present application will be described in detail with reference to the accompanying drawings.

The accompanying drawings illustrate exemplary embodiments of the present application, which are provided only to aid in understanding the present application, and the technical scope of the present application is not limited thereto.

The present application relates to a selective distillation apparatus in which two distillation columns are configured to be switchable between a serial connection mode and a parallel connection mode. Specifically, the selective distillation apparatus of the present application allows a selective operation of high-efficiency operation through a serial connection and high-capacity operation through a parallel connection depending on the situation without removal or addition of any equipment.

The serial connection mode in the present application connects the first distillation column and the second distillation column in a serial connection state, which may mean a structure that the bottom and/or lower part of the first distillation column and the top and/or upper part of the second distillation column are fluidly connected through the pipe, low-boiling substances are separated from the top or upper part of the first distillation column and high-boiling substances are separated from the bottom or lower part of the second distillation column. In addition, the parallel connection mode according to the present application connects the first distillation column and the second distillation column in a parallel connection state, which may mean a structure in which the first distillation column and the second distillation column can separate and discharge low-boiling substances and high-boiling substances, respectively.

In this specification, the "high-boiling substance" may mean a substance having a relatively high boiling point relative to other substances in a mixture, and the "low-boiling substance" may mean a substance having a relatively low boiling point relative to other substances in a mixture. The high-boiling substance may mean a substance having a boiling point of −120° C. or higher or −110° C. or higher at room temperature (25° C.) and normal pressure (1 atm), and the upper limit is not particularly limited. The low-boiling substance may have a boiling point of 200° C. or lower at room temperature (25° C.) and normal pressure (1 atm), and the lower limit is not particularly limited. The boiling point may mean a boiling point of a substance, which may be the same or different depending on the kind of the substance and may vary depending on the temperature and/or the pressure. The high-boiling substance and the low-boiling substance can be divided by the difference in the relative boiling points. In this specification, the high-boiling substance may be a substance having a relatively high boiling point relative to the low-boiling substance at a temperature and a pressure for separating the mixture, and the low-boiling substance may mean a substance having a relatively low boiling point relative to the high-boiling substance at a temperature and a pressure for separating the mixture.

In this specification, the "upper" means a relatively upper portion in the distillation column, and more specifically, when the distillation column is bisected perpendicularly to the longitudinal direction, for example, the length or height direction of the distillation column, it may mean the upper part of the divided two areas. In addition, the ""lower" means a relatively lower portion in the distillation column, and more specifically, when the distillation column is bisected perpendicularly to the longitudinal direction, for example, the length or height direction of the distillation column, it may mean the lower part of the divided two areas. Furthermore, the "top" of the distillation column means the uppermost portion of the distillation column, which may be located at the upper part of the distillation column as described above, and the "bottom" of the distillation column means the lowermost portion of the distillation column, which may be located at the lower part of one distillation column as described above.

FIG. 2 schematically illustrates a structure of a selective distillation apparatus according to one embodiment of the present application. Referring to FIG. 2, the selective distillation apparatus according to the present application may comprise a distillation column (102) equipped with a top reflux device (132) and a bottom reboiler (192), wherein a top outlet and a bottom outlet are formed, an upper inlet and an upper outlet are formed and a lower inlet is formed; a second distillation column (202) equipped with a top reflux device (272) and a bottom reboiler (222), wherein a top outlet and a bottom outlet are formed and an upper inlet and a lower inlet are formed; a piping system and a control part.

The piping system may comprise: a first supply line (12) capable of supplying a raw material to the first distillation column; a second supply line (22) capable of supplying a raw material to the second distillation column; a first connecting line (152+172) connecting the bottom outlet of the first distillation column and the lower inlet of the second distillation column, a second connecting line (152+162) connecting the bottom outlet of the first distillation column and the upper inlet of the second distillation column; and a third connecting line (242+252) connecting the top outlet of the second distillation column and the lower inlet of the first distillation column.

The piping system may comprise a first discharge line (142) connected to the top outlet or upper outlet of the first distillation column so as to be capable of discharging a top product or an upper product of the first distillation column; and a second discharge line (292) connected to the top outlet of the second distillation column so as to be capable of discharging a top product of the second distillation column.

Also, in one example, the piping system may further comprise a fourth connecting line (312+322) connecting the top outlet of the second distillation column (202) and the upper inlet of the first distillation column (102).

The control part may adjust at least one of the reflux devices, the reboilers, the supply lines, the discharge lines, and the connecting lines to an activated or inactivated state. The control part controls a flow of a fluid through open and closure of the piping system, and activates or inactivates equipments such as a reboiler and a reflux device connected to the distillation column, whereby it is possible to switch between the serial connection mode and the parallel connection mode.

FIG. 3 is a diagram illustratively showing a serial connection mode in a selective distillation apparatus according to an embodiment of the present application. In one example, in the serial connection mode of the selective distillation apparatus according to the present application, the second supply line (1021), the second connecting line (1151+1161) and the third connecting line (1241+1251) may be activated, the top reflux device (1131) of the distillation column (1101) and the bottom reboiler (1221) of the second distillation column (1201) may be activated, the first supply line (1011) and the first connecting line (1151+1171) may be inactivated, and the bottom reboiler (1191) of the first distillation column (1101) and the top reflux device (1271) of the second distillation column (1201) may be inactivated. In the serial connection mode, the bottom condensate of the first distillation column (1101) may be introduced into the second distillation column (1201) through the second connecting line (1151+1161) and the top vapor of the second distillation column (1201) may be introduced into the first distillation column (1101) through the third connecting line (1241+1251).

The serial connection mode may have the same efficiency as the sum of the number of stages of the first distillation column (1101) and the number of stages of the second distillation column (1201) and may have an effect that a rectifying section is lengthened by supplying a raw material to the second distillation column. Thus, the serial connection mode may improve the thermodynamic efficiency to separate the product of high purity.

FIG. 4 is a diagram illustratively showing a parallel connection mode in a selective distillation apparatus according to an embodiment of the present application. In one example, in the parallel connection mode of the selective distillation apparatus according to the present application, the first supply line (1012) and the first connecting line (1152+1172) may be activated, the top reflux device (1132) of the first distillation column (1102), the bottom reboiler (1192) of the first distillation column (1102) and the top reflux device (1272) and the bottom reboiler (1222) of the second distillation column (1202) may be activated and the second supply line (1022), the second connecting line (1152+1162) and the third connecting line (1242+1252) may be inactivated. The parallel connection mode may replace the second supply line (1022) by introducing a part of the bottom condensate of the first distillation column (1102) into the second distillation column (1202) through the first connecting line (1152+1172).

FIG. 5 is a diagram illustratively showing a parallel connection mode in a selective distillation apparatus according to another embodiment of the present application.

In the above example, in the parallel connection mode, the first supply line (1013), the first connecting line (1153+1173) and the fourth connecting line (1313+1323) may be activated, the top reflux device (1133) of the first distillation column (1103) and the top reflux device (1273) and the bottom reboiler (1223) of the second distillation column (1203) may be activated, the second supply line (1023), the second connecting line (1153+1163) and the third connecting line (1243+1253) may be inactivated and the bottom reboiler (1193) of the first distillation column (1103) may be inactivated. The parallel connection mode may replace the second supply line (1023) by introducing the bottom condensate of the first distillation column (1103) into the second distillation column (1203) through the first connecting line (1153+1173), and may introduce a part of the top vapor of the second distillation column (1203) condensed through the top reflux device (1273) of the second distillation column into the first distillation column (1103) through the fourth connecting line (1313+1323).

The parallel connection mode may supply the bottom condensate of the first distillation column to the second distillation column to distill it into a state where a relatively high-boiling substance is condensed. In addition, by condensing the vapor of the second distillation column and introducing a part thereof into the upper portion of the first distillation column, there may be an effect that the stripping section is lengthened, thereby enabling the operation control of the first distillation column, even when the reboiler of the distillation column is inactivated. Furthermore, by separating the low-boiling substances from the first discharge lines (1142, 1143) and the second discharge lines (1292, 1293) of the first distillation columns (1102, 1103) and the second distillation columns (1202, 1203) simultaneously, the throughput of the distillation column can be greatly increased, thereby enabling high-capacity operation.

The selective distillation apparatus according to the present application can successively switch between the serial connection mode and the parallel connection mode. The switching can be performed through activation and inactivation of the pipes, thereby enabling successive switching between the serial connection mode and the parallel connection mode without shutdown. Thus, the economic loss that may occur upon the shutdown can be reduced.

The present application also relates to a distillation method using the selective distillation apparatus. The distillation method according to the present application may separate the raw material into a low-boiling substance and a high-boiling substance by controlling at least one of reflux devices, reboilers, supply lines, discharge lines and connecting lines of the selective distillation apparatus in an activated or inactivated state and may distill the raw material and discharge the product by connecting the first distillation column and the second distillation column in a serial connection mode or a parallel connection mode. The product may mean a low-boiling substance flowing out of the top or upper part of the first distillation column and/or the second distillation column and a high-boiling substance flowing out of the bottom of the first distillation column and/or the second distillation column.

In the distillation method of the present application, the detailed description of the selective distillation apparatus is the same as described in the above-mentioned selective distillation apparatus, and thus will be omitted.

The distillation method of the serial connection mode according to one embodiment of the present application may be controlled so that a raw material is introduced into the second supply line, the first supply line, the first connecting line, the bottom reboiler of the first distillation column and the top reflux device of the second distillation column are inactivated, the low-boiling substance is discharged from the top or upper part of the first distillation column and the high-boiling substance is discharged from the bottom of the second distillation column.

In the serial connection mode, a raw material may be supplied to the second distillation column through the second supply line, the raw material may be distilled in the first distillation column and the second distillation column, and the bottom condensate of the first distillation column may be introduced into the second distillation column through the second connecting line and the top vapor of the second distillation column may be introduced into the first distillation column through the third connecting line. Also, the top vapor of the first distillation column is condensed and refluxed using the top reflux device of the first distillation column and the bottom condensate of the second distillation column is heated and introduced into the second distillation column using the bottom reboiler of the second distillation column, whereby the first distillation column and the second distillation column can be operated as a single column. In the serial connection mode, the amount of heat supplied to the reboiler of the first distillation column may be 0 to 40 Gcal/hr, 0 to 30 Gcal/hr, or 0 to 20 Gcal/hr. In addition, the amount of heat supplied to the reboiler of the second distillation column may be 1 to 40 Gcal/hr, 1 to 30 Gcal/hr or 1 to 20 Gcal/hr. The step of serial connection and distillation can be operated at high efficiency using high thermodynamic efficiency.

The distillation method of the parallel connection mode according to one embodiment of the present application may be controlled so that a raw material is introduced into the first supply line, the second connecting line and the third connecting line are inactivated, the low-boiling substance is discharged from the top or upper part of the first distillation column and the second distillation column, and the high-boiling substance is discharged from the bottom of the second distillation column.

In the parallel connection mode, a raw material may be supplied to the first distillation column through the first supply line, the raw material may be distilled in the first distillation column and the second distillation column, and the bottom condensate of the first distillation column may be introduced into the second distillation column through the first connecting line. The parallel connection mode may replace the second supply line by supplying a part of the bottom condensate of the first distillation column the second distillation column through the first connecting line and may separate the low-boiling substances of the first distillation column and the second distillation column simultaneously, whereby the throughput of the distillation column can be greatly increased to enable high-capacity operation.

In the parallel connection mode, "a part" of the bottom condensate of the first distillation column refers to a state where a stream of a fluid through the first connecting line is present in a stream of a fluid flowing out through the bottom outlet of the first distillation column, where the ratio (A/B) of, for example, a bottom stream (A) flowing into the bottom reboiler of the first distillation column to a stream (B) flowing into the second distillation column through the first connecting line may be 0 or more. When the ratio (A/B) is 0, it may mean a state where the bottom condensate of the first distillation column is not introduced into the bottom reboiler of the first distillation column. The upper limit of the ratio (A/B) of the bottom stream (A) flowing into the bottom reboiler of the first distillation column to the stream (B) flowing into the second distillation column through the first connecting line is not particularly limited, and for example, may be 10 or less. In the parallel connection mode, the amount of heat supplied to the reboiler of the first distillation column may be 0 to 40 Gcal/hr, 0 to 30 Gcal/hr, or 0 to 20 Gcal/hr. Also, the amount of heat supplied to the reboiler of the second distillation column may be 1 to 40 Gcal/hr, 1 to 30 Gcal/hr or 1 to 20 Gcal/hr.

The distillation method of the parallel connection mode according to another embodiment of the present application may be controlled so that a raw material is introduced into the first supply line, the second connecting line, the third connecting line and the first reboiler are inactivated, a part of the top vapor condensate of the second distillation column is introduced into the first distillation column through the fourth connecting line, the low-boiling substance is discharged from the top or upper part of the first distillation column and the second distillation column and the high-boiling point substance is discharged from the bottom of the second distillation column.

In the parallel connection mode, a raw material may be supplied to the first distillation column through the first supply line, the raw material may be distilled in the first distillation column and the second distillation column, the bottom condensate of the first distillation column may be introduced into the second distillation column through the first connecting line, a part of the outflow stream of the top reflux device of the second distillation column may be refluxed to the second distillation column through the fourth connecting line and the remaining part may be refluxed to the first distillation column. The parallel connection may replace the second supply line by supplying the bottom condensate of the first distillation column to the second distillation column through the first connecting line and may separate the low-boiling substances of the first distillation column and the second distillation column simultaneously, whereby the throughput of the distillation column can be greatly increased to enable high-capacity operation. Also, by introducing a part of the outflow stream in the top reflux device of the second distillation column into the upper portion of the first distillation column, it is possible to enable the operation control of the first distillation column, even when the reboiler of the distillation column is inactivated.

In the parallel connection mode, "a part" of the outflow stream of the top reflux device of the second distillation column refers to a state where a stream of a fluid through the fourth connecting line is present in a stream of a fluid flowing out of the top reflux device of the second distillation column, where the ratio (C/D) of, for example, a stream (C) flowing into the first distillation column through the fourth connecting line to a stream (D) refluxed from the top reflux device of the second distillation column to the second distillation column may be 0 or more. If the ratio (C/D) is 0, it may mean a state where the outflow stream of the top reflux device of the second distillation column is not introduced into the first distillation column through the fourth connecting line. The upper limit of the ratio (C/D) of the stream (C) flowing into the first distillation column through the fourth connecting line to the stream (D) refluxed from the top reflux device of the second distillation column to the second distillation column is not particularly limited, and for example, may be 10 or less. In the parallel connection mode, the amount of heat supplied to the reboiler of the first distillation column may be 0 to 40 Gcal/hr, 0 to 30 Gcal/hr, or 0 to 20 Gcal/hr. Also, the amount of heat supplied to the reboiler of the second distillation column may be 1 to 40 Gcal/hr, 1 to 30 Gcal/hr or 1 to 20 Gcal/hr.

The distillation method according to the present application can be used in a distillation process of separating a mixture of binary system or more into a high-boiling substance and a low-boiling substance by the difference in boiling points. In one example, the distillation method according to the present application can effuse the product which satisfies Equation 1 below.

$$5°\ C. \leq |BpH-BpL| \leq 65°\ C. \quad \text{[Equation 1]}$$

In Equation 1 above, BpH is a boiling point of a high-boiling substance, and BpL is a boiling point of a low-boiling substance.

In Equation 1 above, the high-boiling substance may mean a product flowing out of the top or upper part of the first distillation column and/or the second distillation column using the distillation method according to the present application, and the low-boiling substance may mean a product a product flowing out of the bottom of the first distillation column and/or the second distillation column using the distillation method according to the present application. The difference (|BpH−BpL|) between the boiling point of the high-boiling substance and the boiling point of the low-boiling substance in Equation 1 above may be 5° C. or higher and 65° C. or lower and may be 10° C. or higher and 65° C. or lower, 10° C. or higher and 60° C. or lower, or 15° C. or higher and 60° C. or lower, but is not limited thereto. In the range satisfying Equation 1 above, the high-efficiency operation of the serial connection mode and the high-capacity operation of the parallel connection mode can be switched as well as the energy efficiency can be improved.

The distillation method according to the present application can be applied to distillation processes of various raw materials. The distillation process may be a process of separating a mixture of alkene and alkane, for example, a process of separating a cracking gas which is a product of a naphtha cracking process. The distillation method according to the present application can be applied to a process of refining ethane as a high-boiling substance and ethylene as a low-boiling substance in the naphtha cracking gas or a process of refining propane as a high-boiling substance and propylene as a low-boiling substance, but is not limited thereto.

In one example, the distillation method according to the present application can be controlled so that the low-boiling substance has a purity of 99 wt % or more, and can also be controlled so that the high-boiling substance has a purity of 99 wt % or more. The upper limit of the purity of the low-boiling substance and the purity of the high-boiling substance is not particularly limited and may be, for example, 100 wt % or less. The distillation method of the present application can satisfy the purity in the serial connection mode and/or the parallel connection mode. By adjusting the reflux ratio of the first distillation column and/or the second distillation column in the serial connection mode and/or the parallel connection mode, it is possible to produce a low-boiling substance and a high-boiling substance in the purity range.

In one example, the distillation method according to the present application can be controlled to satisfy Equation 2 below.

$$P/Rd \geq 3700 \quad \text{[Equation 2]}$$

In Equation 2, P is a yield per hour (kg·hr) of the low-boiling substance and Rd is a heat quantity per hour (Gcal/hr) supplied to the reboiler of the distillation column.

In Equation 2 above, the upper limit of P/Rd is not particularly limited, and may be, for example, 20,000 or less.

The distillation method according to the present application can satisfy Equation 1 above by supplying a part of the bottom condensate of the first distillation column to the second distillation column, whereby the processing capacity of the distillation column can be greatly increased to control the decrease in energy efficiency with a small width, even if the high-capacity operation is performed.

Hereinafter, the present application will be described in detail by way of examples according to the present application, but the scope of the present application is not limited by the following examples.

Example 1

Ethylene and ethane were separated from the C2 component produced in the naphtha cracking process using the selective distillation apparatus illustrated in FIG. 2.

As illustrated in FIG. 3, in the serial connection mode, the second supply line (1021), the second connecting line (1151+1161) connecting the bottom outlet of the first distillation column (1101) and the upper inlet of the second distillation column (1201), the third connecting line (1241+1251) connecting the top outlet of the second distillation column (1201) and the lower inlet of the first distillation column (1101) and the first connecting line (1141) connected to the upper outlet of the first distillation column (1101) were activated, the top outlet of the first distillation column (1101) was connected to the top reflux device (1131) of the first distillation column (1101) and the top reflux device (1131) of the first distillation column (1101) was connected to the upper inlet of the first distillation column (1101). The bottom outlet of the second distillation column (1201) was connected to the bottom reboiler (1221) of the second distillation column (1201) and the bottom reboiler (1221) of the second distillation column (1201) was connected to the lower inlet of the second distillation column (1201). The top reflux device (1131) of the first distillation column (1101) and the bottom reboiler (1221) of the second distillation column were activated and the bottom reboiler (1191) of the first distillation column (1101) and the top reflux device (1271) of the second column (1201) were inactivated.

In the selective distillation apparatus of the serial connection mode, the raw material was supplied at a flow rate of 59,104 kg/hr to the second distillation column (1201) through the second supply line (1021), the bottom condensate of the first distillation column (1101) was introduced to the second distillation column (1201) through the second connecting line (1151+1161), and the top vapor of the second distillation column (1201) was introduced into the first distillation column (1101) through the third connecting line (1241+1251). The bottom condensate of the second distillation column (1201) was heated through the bottom reboiler (1221) of the second distillation column and the top vapor of the first distillation column (1101) was condensed and refluxed through the top reflux device (1131) of the first distillation column. Ethylene as a low-boiling substance was separated into the first discharge line (1141) of the first distillation column (1101) and ethane as a high-boiling substance was separated from the bottom of the second distillation column (1201). In the serial connection mode, the temperature of the top was −36.24° C., the pressure was maintained at 15.54 kg/cm², the energy supply quantity through the reboiler was 10.18 Gcal/hr, and the reflux ratio was controlled to 5.33.

Example 2

As illustrated in FIG. 4, in the parallel connection mode, the first supply line (1012), the first connecting line (1152+1172) connecting the bottom outlet of the first distillation column (1102) and the lower inlet of the second distillation column (1202), and the first discharge line (1142) connected to the upper outlet of the first distillation column (1102) were activated, the top outlet of the first distillation column (1102)

was connected to the top reflux device (1132) of the first distillation column (1102), and the top reflux device (1132) of the first distillation column (1102) was connected to the upper inlet of the first distillation column (1102). The bottom outlet of the second distillation column (1202) was connected to the bottom reboiler (1222) of the second distillation column (1202) and the bottom reboiler (1222) of the second distillation column (1202) was connected to the lower inlet of the second distillation column (1202). The top reflux device (1132) and the bottom reboiler (1191) of the first distillation column (1102) and the bottom reboiler (1222) of the second distillation column (1202) were activated.

In the selective distillation apparatus of the parallel connection mode, the raw material was introduced at a flow rate of 80,000 kg/hr into the first distillation column (1102) through the first supply line (1012), and a part (1152) of the bottom condensate of the first distillation column (1102) was introduced at a flow rate of 58,500 kg/hr into the second distillation column (1202) through the first connecting line (1152+172). The bottom condensate was heated in the bottom reboiler (1192) of the first distillation column (1102) and the bottom reboiler (1222) of the second distillation column (1202), and the top vapor was condensed and refluxed from the top reflux device (1132) of the first distillation column and the top reflux device (1272) of the second distillation column. Ethylene as the low-boiling substance was separated into the first discharge line (1142) of the first distillation column (1102) and the second discharge line (1292) of the second distillation column (1202) and ethane as the high-boiling substance was separated from the bottom of the second distillation column (1202). In the parallel connection mode, when the energy supply quantity through the reboiler of the first distillation column was 1 Gcal/hr, the energy supply quantity through the reboiler of the second distillation column was maintained at 14.95 Gcal/hr, and when the energy supply quantity through the reboiler of the first distillation column was 6 Gcal/hr, the energy supply quantity through the reboiler of the second distillation column was maintained at 11.41 Gcal/hr, and the reflux ratio was controlled so that the reflux ratio of the first distillation column was 4.18, and the reflux ratio of the second distillation column was 3.06. In the parallel connection mode, the temperature of the top was −36.24° C. and the pressure was maintained at 15.54 kg/cm$^2$. When the total production amount was kept constant in the parallel connection mode, the energy supply quantities through the reboilers of the first distillation column and the second distillation column and the production amounts of the first distillation column and the second distillation column were shown in Table 1 below.

Example 3

As illustrated in FIG. 5, the same device configuration as in Example 2 was used except that in the parallel connection mode, the fourth connecting line (1313+1323) connecting the upper inlet of the first distillation column (1103) and the top outlet of the second distillation column (1203) was activated and the bottom reboiler (1193) of the first distillation column (1103) was inactivated. Ethylene and ethane were separated in the same manner as in Example 2 except that all the bottom condensate of the first distillation column (1103) was introduced into the second distillation column (1203) through the first connecting line (1153+1173) and a stream of 5 kg/hr in the outflow stream of the top reflux device (1273) of the second distillation column (1203) was introduced into the first distillation column (1103) through the fourth connecting line (1313+1323) and the energy supply quantity through the bottom reboiler of the second distillation column was 15.72 Gcal/hr.

TABLE 1

| | <Example> | | | |
|---|---|---|---|---|
| | 1 | 2-1 | 2-2 | 3 |
| First Distillation Column Production Amount(kg/hr) | 48,466 | 21,256 | 34,342 | 18,609 |
| Second Distillation Column Production Amount(kg/hr) | — | 44,338 | 31,252 | 46,985 |
| Production Amount (kg/hr) | 48,466 | 65,594 | 65,594 | 65,594 |
| First Distillation Column Reboiler Duty (Gcal/hr) | 0 | 1 | 6 | 0 |
| Second Distillation Column Reboiler Duty (Gcal/hr) | 10.18 | 14.95 | 11.41 | 15.72 |
| Total Reboiler Duty (Gcal/hr) | 10.18 | 15.95 | 17.41 | 15.72 |
| Ethylene Concentration (%) | 99.96 | 99.96 | 99.96 | 99.96 |

As shown in Examples and Table 1, when the distillation column is operated using the selective distillation apparatus according to Examples of the present application, high-efficiency operation and high-capacity operation can be selectively operated without changing the equipments.

The invention claimed is:

1. A selective distillation apparatus comprising: a first distillation column equipped with a top reflux device and a bottom reboiler, wherein a top outlet and a bottom outlet are formed, an upper inlet and an upper outlet are formed and a lower inlet is formed; a second distillation column equipped with a top reflux device and a bottom reboiler, wherein a top outlet and a bottom outlet are formed and an upper inlet and a lower inlet are formed; a piping system and a control part,
   wherein said piping system comprises: a first supply line capable of supplying a raw material to said first distillation column; a second supply line capable of supplying a raw material to said second distillation column; a first discharge line capable of discharging a top product or an upper product of said first distillation column; a second discharge line capable of discharging a top product of said second distillation column; a first connecting line connecting the bottom outlet of said first distillation column and the lower inlet of the second distillation column; a second connecting line connecting the bottom outlet of said first distillation column and the upper inlet of the second distillation column; a third connecting line connecting the top outlet of said second distillation column and the lower inlet of the first distillation column; and a fourth connecting line connecting the top outlet of said second distillation column and the upper inlet of the first distillation column, and
   wherein said control part is configured to adjust at least one operating state of the reflux devices, the reboilers, the supply lines, the discharge lines, and the connecting lines to an activated or inactivated state,
   wherein the control part is configured to inactivate the first supply line, the first connecting line, the bottom reboiler of the first distillation column and the top reflux device of the second distillation column when the raw material is supplied to the second supply line, or wherein the control part is configured to inactivate the second connecting line and the third connecting line when the raw material is supplied to the first supply line, or wherein the control part is configured to inactivate the second connecting line, the third connecting line and the bottom reboiler of the first distillation column when the raw material is supplied to the first supply line.

2. A distillation method of a raw material using the selective distillation apparatus of claim 1, wherein the method comprises: a first step of controlling at least one of the reflux devices, the reboilers, the supply lines, the discharge lines and the connecting lines of said selective distillation apparatus in an activated or inactivated state; and a second step of discharging products while maintaining the connection state of the first and second distillation columns in a serial connection or parallel connection state.

3. The distillation method according to claim 2, wherein the first step comprises introducing the raw material into the second supply line in a state where the first supply line, the first connecting line, the bottom reboiler of the first distillation column and the top reflux device of the second distillation column are inactivated; and wherein the second step comprises discharging products from the top or upper part of the first distillation column and the bottom of the second distillation column.

4. The distillation method according to claim 2, wherein the first step comprises introducing the raw material into the first supply line in a state where the second connecting line and the third connecting line are inactivated; and wherein the second step comprises discharging products from the top or upper part of the first distillation column and the second distillation column and the bottom of the second distillation column.

5. The distillation method according to claim 2, wherein the first step comprises introducing the raw material into the first supply line in a state where the second connecting line, the third connecting line and the bottom reboiler of the first distillation column are inactivated; and introducing a part of the outflow stream of the top reflux device of the second distillation column into the first distillation column through the fourth connecting line; and wherein the second step comprises discharging products from the top or upper part of the first distillation column and the second distillation column and the bottom of the second distillation column.

6. The distillation method according to claim 2, wherein the product satisfies Equation 1 below $$5° C. \leq |BpH-BpL| \leq 65° C.,$$ [Equation 1]

wherein, BpH is a boiling point of a high-boiling substance, and BpL is a boiling point of a low-boiling substance.

7. The distillation method according to claim 6, wherein said low-boiling substance is alkene and the high-boiling substance is alkane.

8. The distillation method according to claim 6, wherein the low-boiling substance and the high-boiling substance have a purity of 99 wt % or more.

9. The distillation method according to claim 6, wherein the method satisfies Equation 2 below:

$$P/Rd \geq 3700,$$ [Equation 2]

wherein P is a yield per hour (kg/hr) of the low-boiling substance and Rd is a heat quantity per hour (Gcal/hr) supplied to the bottom reboilers of the first and second distillation columns.

* * * * *